US012708448B2

(12) United States Patent
Mariampillai

(10) Patent No.: US 12,708,448 B2
(45) Date of Patent: Aug. 18, 2026

(54) SURFACE DETECTION DEVICE WITH INTEGRATED REFERENCE FEATURE AND METHODS OF USE THEREOF

(71) Applicant: 7D SURGICAL ULC, Toronto (CA)

(72) Inventor: Adrian Mariampillai, Toronto (CA)

(73) Assignee: 7D SURGICAL ULC, Ontario (CA)

( * ) Notice: Subject to any disclaimer, the term of this patent is extended or adjusted under 35 U.S.C. 154(b) by 458 days.

(21) Appl. No.: 17/920,589

(22) PCT Filed: Apr. 20, 2021

(86) PCT No.: PCT/CA2021/050537
§ 371 (c)(1),
(2) Date: Oct. 21, 2022

(87) PCT Pub. No.: WO2021/212218
PCT Pub. Date: Oct. 28, 2021

(65) Prior Publication Data

US 2023/0149096 A1 May 18, 2023

Related U.S. Application Data

(60) Provisional application No. 63/013,860, filed on Apr. 22, 2020.

(51) Int. Cl.
*A61B 34/20* (2016.01)
*G06T 7/10* (2017.01)
(Continued)

(52) U.S. Cl.
CPC ................ *A61B 34/20* (2016.02); *G06T 7/10* (2017.01); *G06T 7/344* (2017.01); *G06T 7/521* (2017.01);
(Continued)

(58) Field of Classification Search
CPC ............ A61B 34/20; A61B 2034/2055; G06T 2207/30204
See application file for complete search history.

(56) References Cited

U.S. PATENT DOCUMENTS 7,567,833 B2 7/2009 Moctezuma De La Barrera et al.
7,927,014 B2 4/2011 Dehler
(Continued)

FOREIGN PATENT DOCUMENTS

WO 2019195926 A1 10/2019

OTHER PUBLICATIONS

The International Search Report for PCT/CA2021/050537 dated Aug. 6, 2021, 4 pages.
(Continued)

*Primary Examiner* — Serkan Akar
*Assistant Examiner* — Gabriel Victor Popescu
(74) *Attorney, Agent, or Firm* — Stephen Leonard; AIRD & BERLIS LLP

(57) ABSTRACT

Systems, devices and methods are provided for facilitating surgical guidance using a surface detection device. In some example embodiments, a trackable surface detection device is disclosed that includes, in a spatially-fixed relationship, a surface detection subsystem, one or more reference markers that are detectable by a tracking system, and an integrated reference feature that is detectable by the surface detection subsystem for calibration thereof. The trackable surface detection device, which may be handheld, facilitates the determination of a calibration transform that relates a frame of reference of the surface detection subsystem to a frame of reference of the tracking system, which in turn may be employed, in combination with a transform obtained by performing surface-to-surface registration of intraoperatively detected surface data and pre-operative image data
(Continued)

pertaining to a subject, when generating an intraoperative display, in a common frame of reference, of the pre-operative image data and a tracked surgical tool.

30 Claims, 9 Drawing Sheets

(51) Int. Cl.

| | |
|---|---|
| ***G06T 7/33*** | (2017.01) |
| ***G06T 7/521*** | (2017.01) |
| *A61B 17/00* | (2006.01) |
| *A61B 90/00* | (2016.01) |

(52) U.S. Cl.
CPC ............... *A61B 2017/00725* (2013.01); *A61B 2034/2048* (2016.02); *A61B 2034/2055* (2016.02); *A61B 2090/3983* (2016.02); *G06T 2207/30004* (2013.01); *G06T 2207/30204* (2013.01)

(56) References Cited

U.S. PATENT DOCUMENTS

| | | | | |
|---|---|---|---|---|
| 10,463,434 | B2 | 11/2019 | Siegler et al. | |
| 10,575,755 | B2 | 3/2020 | Breisacher et al. | |
| 2011/0069867 | A1* | 3/2011 | Buehner ................ | A61B 90/39 382/103 |
| 2019/0350658 | A1 | 11/2019 | Yang et al. | |
| 2020/0193622 | A1* | 6/2020 | Stopp ..................... | A61B 90/39 |
| 2020/0305982 | A1* | 10/2020 | Akbarian .............. | A61B 34/20 |

OTHER PUBLICATIONS

Lai Marco et al "Fusion of augmented reality imaging with the endoscopic view for endonasal skull base surgery; a novel application for surgical navigation based on intraoperative cone beam computed tomography and optical tracking", PLOS ONE, vol. 15, No. 1, Jan. 16, 2020, XP093052047, DOI: 10.1371/journal.pone.0227312 Retrieved from the Internet: URL:https://www.ncbi.nlm.nih.gov/pmc/artic les/PMC6964902/pdf/pone.0227312.pdf>.

* cited by examiner

SURFACE DETECTION DEVICE WITH INTEGRATED REFERENCE FEATURE AND METHODS OF USE THEREOF

CROSS-REFERENCE TO RELATED APPLICATION

This application is a National Phase application claiming the benefit of the international PCT Patent Application No. PCT/CA2021/050537, filed on Apr. 20, 2021, in English, which claims priority to U.S. Provisional Patent Application No. 63/013,860, titled "SURFACE DETECTION DEVICE WITH INTEGRATED REFERENCE FEATURE AND METHODS OF USE THEREOF" and filed on Apr. 22, 2020, the entire contents of which are incorporated herein by reference.

BACKGROUND

The present disclosure relates to image-guided surgical navigation. More particularly, the present disclosure relates to image-guided surgical navigation of spinal procedures using intraoperative surface detection.

Surgical navigation facilitates the intraoperative display, in a common intraoperative frame of reference, of preoperative patient image data and tracked surgical instruments. Many techniques exist for determining the appropriate coordinate transformations ("transforms") required for surgical navigation, such as the use of fiducial markers and tracking systems.

Some navigation systems employ the combined use of a surface detection system and a tracking system to facilitate surgical navigation. In such implementations, the surface detection system is used to collect intraoperative surface data associated with an anatomical surface of the patient. Surface-to-surface image registration, performed between the intraoperative surface data and pre-operative surface data (segmented from the pre-operative image data), may then be employed to determine a transform between the frame of reference of the pre-operative image data and the intraoperative frame of reference of the surface detection system. A calibration transform, relating the intraoperative frame of reference of the surface detection system and the intraoperative frame of reference of the tracking system, may then be employed to facilitate the combined representation of the pre-operative image data and tracked surgical tools in a common intraoperative frame of reference.

SUMMARY

Systems, devices and methods are provided for facilitating surgical guidance using a surface detection device. In some example embodiments, a trackable surface detection device is disclosed that includes, in a spatially-fixed relationship, a surface detection subsystem, one or more reference markers that are detectable by a tracking system, and an integrated reference feature, such as a reference surface or reference marker, that is detectable by the surface detection subsystem for calibration thereof. The trackable surface detection device, which may be handheld, facilitates the determination of a calibration transform that relates a frame of reference of the surface detection subsystem to a frame of reference of the tracking system, which in turn may be employed, in combination with a transform obtained by performing surface-to-surface registration of intraoperatively detected surface data and pre-operative image data pertaining to a subject, when generating an intraoperative display, in a common frame of reference, of the pre-operative image data and a tracked surgical tool.

Accordingly, in a first aspect, there is provided a trackable surface detection device comprising:

- a surface detection subsystem;
- a reference feature rigidly supported relative to said surface detection subsystem, said reference feature being positioned to be detectable by said surface detection subsystem; and
- at least one tracking marker rigidly supported relative to said surface detection subsystem.

In some example implementations, the device further comprises a housing, said housing supporting said surface detection subsystem. The housing may be configured to be supported in a handheld configuration. At least a portion of the reference feature may be rigidly supported within said housing. The distal region of the housing may include an aperture, and wherein at least a portion of said reference feature is peripherally disposed around at least a portion of said aperture.

At least a portion of the reference feature may be rigidly supported beyond a distal end of said housing. The reference feature may be rigidly supported beyond a distal end of said housing. The surface detection subsystem may have a depth of field for surface detection that resides, at least in part, beyond a distal end of said housing, and wherein said reference feature resides within the depth of field of said surface detection subsystem.

In some implementations of the device, the surface detection subsystem is a structured light surface detection subsystem.

In some implementations of the device, the reference feature comprises a reference surface detectable by said surface detection subsystem.

In another aspect, there is provided a medical navigation system comprising:

- a trackable surface detection device as described above, including a reference surface;
- a tracking system configured to detect said at least one tracking marker;
- control and processing circuitry operatively coupled to said surface detection subsystem and said tracking system, said control and processing circuitry comprising at least one processor and associated memory, said memory comprising instructions executable by said at least one processor for performing operations comprising:
  - controlling said tracking system and said surface detection subsystem to:
    - acquire surface data; and
    - detect tracking signals associated with said at least one tracking marker;
  - processing the tracking signals to obtain first location information suitable locating said at least one tracking marker within a coordinate system of said tracking system; and
  - processing the first location information, the surface data, and calibration data, to determine a calibration transform relating a coordinate system of said surface detection subsystem to the coordinate system of said tracking system;
  - the calibration data comprising three-dimensional model data characterizing said reference surface and second location information suitable for locating said reference surface relative to said at least one tracking marker.

In some example implementations of the system, the control and processing circuitry is configured to generate the calibration transform by: employing the first location information and the second location information to represent the three-dimensional model data within the coordinate system of said tracking system; and performing surface-to-surface registration between the surface data and the three-dimensional model data represented within the coordinate system of said tracking system, thereby obtaining the calibration transform. The control and processing circuitry may be configured to: segment the surface data to obtain reference surface data associated with said reference surface; and employ the reference surface data when performing surface-to-surface registration.

In some example implementations of the system, the control and processing circuitry is configured to generate the calibration transform by: representing the three-dimensional model data and the surface data within an initial coordinate system that is fixed relative to a frame of reference of the trackable surface detection device; within the initial coordinate system, performing surface-to-surface registration between the surface data and the three-dimensional model data, thereby obtaining a preliminary calibration transform; and employing the first location information, the preliminary calibration transform, and the second location information to determine the calibration transform. The initial coordinate system may be the coordinate system of the surface detection subsystem.

In some example implementations of the system, the surface data and the tracking signals are obtained simultaneously, and wherein the control and processing circuitry is further configured to: employ surface-to-surface registration between (i) the surface data and (ii) pre-operative surface data generated from pre-operative volumetric image data associated with the subject, to determine an intraoperative transform; and employ the intraoperative transform and the calibration transform to represent the pre-operative volumetric image data and one or more tracked medical instruments within a common frame of reference.

In some example implementations of the system, the surface data is first surface data, wherein the control and processing circuitry is further configured to: acquire second surface data simultaneously with acquisition of the tracking signals; employ surface-to-surface registration between (i) the second surface data and (ii) pre-operative surface data generated from pre-operative volumetric image data associated with the subject, to determine an intraoperative transform; and employ the intraoperative transform, and the calibration transform to represent the pre-operative volumetric image data and one or more tracked medical instruments within a common frame of reference.

In some example implementations of the system, the trackable surface detection device further comprises a motion sensor, the motion sensor being operatively coupled to the control and processing circuitry, wherein the control and processing circuitry is further configured to: process motion sensor signals obtained from the motion sensor; and reject the calibration transform when the motion sensor signals, or a measure associated therewith satisfy motion criteria.

In some example implementations of the system, the trackable surface detection device further comprises a means for signaling, to one or both of the tracking system and the control and processing circuitry, the acquisition of the surface data.

In another aspect, there is provided a surface detection device comprising:

- a surface detection subsystem; and
- a reference feature rigidly supported relative to the surface detection subsystem, the reference feature being positioned to be detectable by the surface detection subsystem.

In another aspect, there is provided a surgical navigation system comprising:

- a tracking system; and
- a trackable surface detection device comprising:
  - a surface detection subsystem;
  - a reference feature rigidly supported relative to the surface detection subsystem, the reference feature being positioned to be detectable by the surface detection subsystem; and
  - at least one tracking marker rigidly supported relative to the surface detection subsystem, the at least one tracking marker being detectable by the tracking system.

In another aspect, there is provided a method of calibrating a surgical navigation system, the surgical navigation system comprising a trackable surface detection device as described above (including a reference surface) and a tracking system, the method comprising:

- controlling the trackable surface detection device to acquire surface data;
- controlling the tracking system to detect tracking signals associated with the at least one tracking marker of the trackable surface detection device;
- processing the tracking signals to obtain first location information suitable locating the at least one tracking marker within a coordinate system of the tracking system; and
- processing the first location information, the surface data, and calibration data, to determine a calibration transform relating a coordinate system of the surface detection subsystem to the coordinate system of the tracking system;
- the calibration data comprising three-dimensional model data characterizing the reference surface and second location information suitable for locating the reference surface relative to the at least one tracking marker.

In some example implementations of the method, the calibration transform is generated by: employing the first location information and the second location information to represent the three-dimensional model data within the coordinate system of the tracking system; and performing surface-to-surface registration between the surface data and the three-dimensional model data represented within the coordinate system of the tracking system, thereby obtaining the calibration transform. The method may further comprise: segmenting the surface data to obtain reference surface data associated with the reference surface; and

- employing the reference surface data when performing surface-to-surface registration.

In some example implementations of the method, the calibration transform is generated by:

- representing the three-dimensional model data and the surface data within an initial coordinate system that is fixed relative to a frame of reference of the surface detection device;
- within the initial coordinate system, performing surface-to-surface registration between the surface data and the three-dimensional model data, thereby obtaining a preliminary calibration transform; and
- employing the first location information, the preliminary calibration transform, and the second location information to determine the calibration transform. The initial coordinate system may be the coordinate system of the surface detection subsystem.

In some example implementations of the method, the surface data and the tracking signals are obtained simultaneously, the method further comprising:

employing surface-to-surface registration between (i) the surface data and (ii) pre-operative surface data generated from pre-operative volumetric image data associated with the subject, to determine an intraoperative transform; and employing the intraoperative transform and the calibration transform to represent the pre-operative volumetric image data and one or more tracked medical instruments within a common frame of reference.

In some example implementations of the method, the surface data is first surface data, the method further comprising: acquiring second surface data simultaneously with acquisition of the tracking signals; employing surface-to-surface registration between (i) the second surface data and (ii) pre-operative surface data generated from pre-operative volumetric image data associated with the subject, to determine an intraoperative transform; and employing the intraoperative transform, and the calibration transform to represent the pre-operative volumetric image data and one or more tracked medical instruments within a common frame of reference.

In another aspect, there is provided a medical navigation system comprising:

a trackable surface detection device provided as described above;

a tracking system configured to detect the at least one tracking marker;

control and processing circuitry operatively coupled to the surface detection subsystem and the tracking system, the control and processing circuitry comprising at least one processor and associated memory, the memory comprising instructions executable by the at least one processor for performing operations comprising:

controlling the surface detection subsystem to acquire reference signals associated with the reference feature; and controlling the tracking system to detect tracking signals associated with the at least one tracking marker;

processing the tracking signals to obtain first location information suitable locating the at least one tracking marker within a coordinate system of the tracking system; and processing the first location information, the reference signals, and calibration data, to determine a calibration transform relating a coordinate system of the surface detection subsystem to the coordinate system of the tracking system;

the calibration data comprising model data characterizing the reference feature and second location information suitable for locating the reference feature relative to the at least one tracking marker.

The surface detection subsystem may be a structured light surface detection system comprising a projector and one or more cameras, and wherein the reference signals are detected by the one or more cameras in absence of illumination by the projector.

In another aspect, there is provided a method of calibrating a surgical navigation system, the surgical navigation system comprising a trackable surface detection device as described above and a tracking system, the method comprising:

controlling the trackable surface detection device to acquire reference signals associated with the reference feature;

controlling the tracking system to detect tracking signals associated with the at least one tracking marker of the trackable surface detection device;

processing the tracking signals to obtain first location information suitable locating the at least one tracking marker within a coordinate system of the tracking system; and processing the first location information, the reference signals, and calibration data, to determine a calibration transform relating a coordinate system of the surface detection subsystem to the coordinate system of the tracking system;

the calibration data comprising model data characterizing the reference feature and second location information suitable for locating the reference feature relative to the at least one tracking marker.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
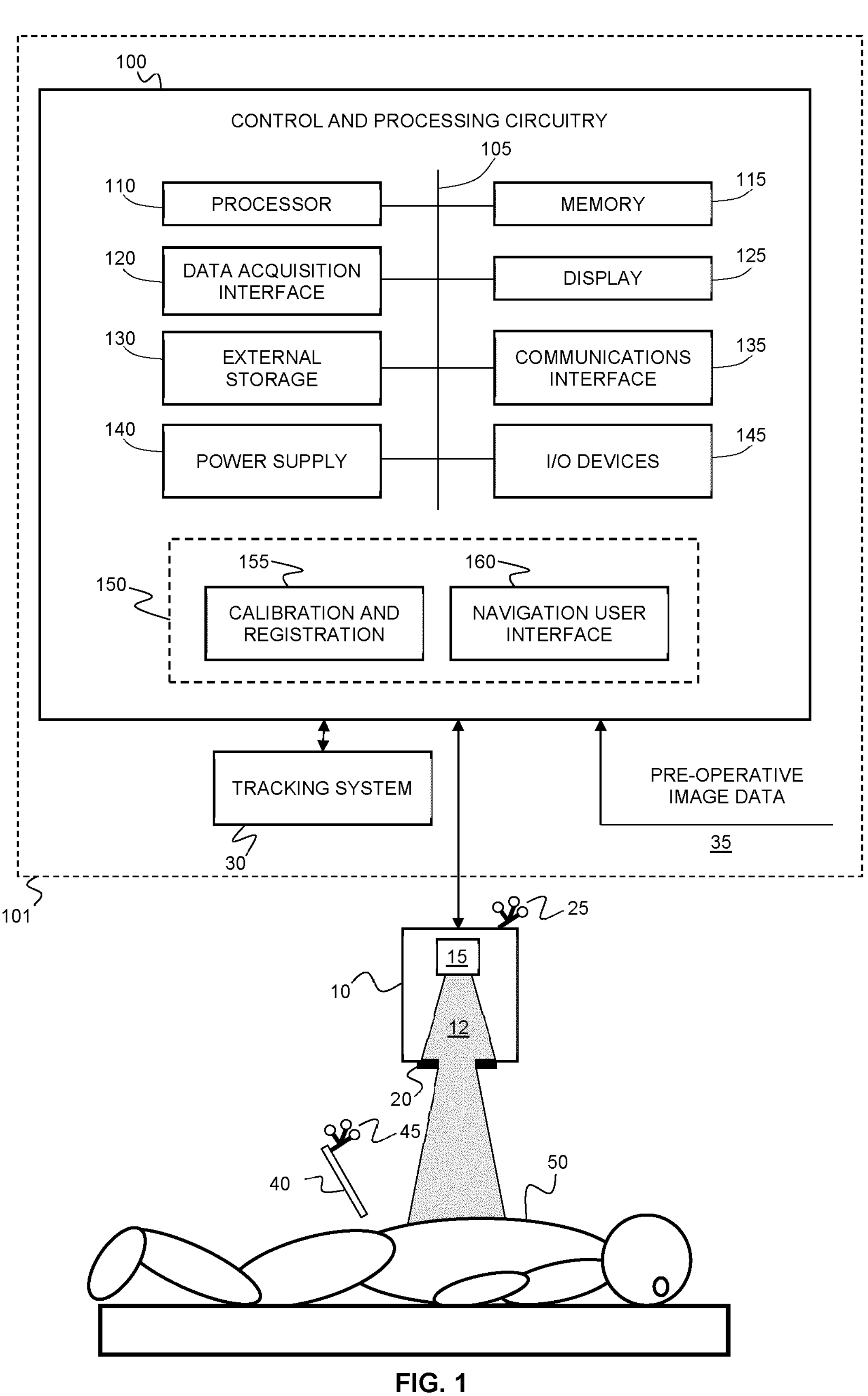
FIG. 1 illustrates an example system for performing intraoperative surface detection and intraoperative image registration for surgical navigation using a trackable surface detection device.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms “comprises” and “comprising” are to be construed as being inclusive and open ended, and not exclusive. Specifically, when used in the specification and claims, the terms “comprises” and “comprising” and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein, the term "tracking marker" refers to a locating indicator that may be affixed or otherwise connected to a handheld implement, patient, subject, instrument, tool, or other component of a surgical system or surgical field, and which is detectable by a tracking system for use in determining a position. A marker may be active or passive, and may be detectable using an optical or electromagnetic detector. An example optical passive marker is a reflective sphere, or portion thereof, and an example active optical marker is an LED. Another example of a marker is a glyph, which may contain sufficient spatial and/or geometrical co-planar features for determining a three-dimensional position and orientation. For example, a glyph marker may include at least three corner features, where the three corner features define a plane.

As used herein, the term "surface detection system" refers to a system that is capable of detecting signals indicative of the topography of a three-dimensional surface (e.g. acquires a set of surface data describing the surface topography) within a field of view. Examples of surface imaging techniques include structured light illumination, laser range finding, and photogrammetry.

As used herein, the terms "calibration transformation" and "calibration transform" refer to a transformation that relates the coordinate system of a surface imaging system to that of a tracking system.

As used herein, the phrase "field of view", when employed in association with a surface detection subsystem, refers to the spatial region over which a surface may be positioned, relative to the surface detection subsystem, for detection of surface data by the surface detection system. For example, the field of view of an example structured light system that includes a structured light projector and two cameras may be determined to span the overlap of (i) the respective fields of view of cameras and (ii) the spatial region within which the structured light is projected. In an example involving a LiDAR-based surface detection system including an optical receiver and a laser scanner, the field of view may be determined based on the spatial overlap between the field of view of the optical receiver and the spatial region within which the laser scanner is capable of scanning the laser.

As explained above, navigation systems that employ the combined use of a surface detection system and a tracking system to facilitate surgical navigation require the use of a calibration transform that relates the frame of reference of the surface detection system and the frame of reference of the tracking system, in order to facilitate the combined representation of the pre-operative image data and tracked surgical tools in a common intraoperative frame of reference. Known surgical navigation systems that include a surface detection system and a tracking system, and utilize surface-to-surface image registration, have been described as employing two different configurations: a rigid configuration in which the surface detection system is rigidly connected to the tracking system, and a decoupled configuration in which the surface detection system includes tracking markers and is not rigidly connected to the tracking system.

In the rigid configuration, the rigid physical connection between the two systems provides an inherent initial calibration transform between the frame of reference of the surface detection system and the frame of reference of the tracking system. In the decoupled configuration, the surface detection system includes tracking markers that facilitate the determination of an initial calibration transform between the frame of reference of the surface detection system and the frame of reference of the tracking system.

The present inventors have found that when using either the rigid or decoupled configurations, the initial calibration transform can be insufficient to provide sufficient accuracy in many clinical applications, leading to image registration and navigation errors due to effects such as mechanical drift in the alignment of the components, for example, due to thermal expansion. For example, if one or more components of the system were to undergo a significant mechanical impact, the relative positioning of the surface imaging system and the tracking system may shift slightly. In another example, the transformation may be dependent on the ambient temperature in which it is operating and thus only valid within a specified range of ambient temperatures.

In order to obtain a more accurate calibration transform, a dedicated calibration device can be employed that includes tracking markers and a reference surface detectable by the surface detection system. According to such methods, the tracking markers of the calibration device are detected by the tracking system and the reference surface is detected by the surface detection system. Image registration is performed to register a three-dimensional model of the reference surface to the reference surface data, and a known fixed spatial relationship between the tracking markers and the reference surface is employed to generate the calibration transform.

The present inventors realized that the need to employ an external calibration device to obtain an accurate calibration transform could be avoided integrating the calibration device and the surface detection system into a trackable surface detection device that includes, in a spatially rigid configuration, a surface detection subsystem, one or more tracking markers, and the reference feature, where the reference feature is positioned such that it is detectable by the surface detection subsystem. Such an integrated device would facilitate surface-detection-based surgical navigation in a decoupled configuration that employs a handheld surface detection device. The integration of the reference feature and the one or more tracking markers with the surface detection subsystem could be beneficial in reducing the overall complexity of the system and potentially improving clinical utility and workflow.

Accordingly, in various example embodiments, a trackable surface detection device is disclosed that includes, in a spatially-fixed relationship, a surface detection subsystem, one or more reference markers that are detectable by a tracking system, and an integrated reference feature that is detectable by the surface detection subsystem for calibration thereof. As explained in detail below, the trackable surface detection device facilitates the determination of an accurate calibration transform that relates a frame of reference of the surface detection subsystem to a frame of reference of the tracking system, without requiring the use of an external calibration device. In some example embodiments, the trackable surface detection device is provided in a handheld configuration.

Referring now to FIG. 1, an example system for performing intraoperative surface detection and intraoperative image registration for surgical navigation using a trackable surface detection device 10. The example system includes a trackable surface detection device 10 that includes a surface detection subsystem 15 (e.g. supported within a housing), one or more tracking markers 25 positioned to be detectable by a tracking system 30, and a reference surface 20 (an example of a reference feature) that is positioned within the field of view 12 of the surface detection subsystem 10. The trackable surface detection device 10 includes a surface detection subsystem 15 suitable system for detecting, measuring, imaging, or otherwise determining the surface topography of one or more objects (such as, but not limited to, a region of an exposed spine of a patient 50). The trackable surface detection device 10 is operably interfaced with control and processing circuitry 100, which is described in further detail below.

The surface detection subsystem 15 may employ any suitable modality for detecting, measuring, imaging, or otherwise determining the surface topography of one or more objects, using, for example, optical radiation or sound waves (e.g. ultrasound). Non-limiting examples of suitable optical devices include laser range finders, photogrammetry systems, and structured light imaging systems, which project surface topography detection light onto a region of interest, and detect surface topography light that is scattered or reflected from the region of interest. The detected optical signals can be used to generate surface topography datasets consisting of point clouds or meshes. Other examples using sound waves for determining surface topography can include ultrasonography.

In some example implementations, the surface detection subsystem 15 employs structured light for surface detection. A structured light detection subsystem may include, for example, at least one projection device and at least one camera (examples of such systems are described in further detail below). The projection device projects temporally and/or spatially modulated light onto the surface to be imaged, while the camera(s) capture images of the surface region illuminated by the projection device. This active illumination enables robust and efficient identification of pixel correspondences between calibrated camera-projector (a projector may be thought of as an inverse camera) or calibrated camera-camera system. The correspondence (disparity) data can then be transformed into real-space coordinate data in the coordinate system of the calibrated camera (s) and/or projection device by geometrical triangulation.

In some example embodiments, the trackable surface detection device 10 is configured to be handheld and may be connected to the control and processing circuitry 100, for example, via a wired connection or a wireless connection (e.g. via a local wireless protocol such as Bluetooth®) facilitated by a wireless transceiver that is operably connected to the surface detection subsystem.

The example system shown in FIG. 1 also includes a tracking system 30 that is operably interfaced with control and processing circuitry 100, and which is employed to track the position and orientation of the trackable surface detection device 10. The trackable surface detection device is shown having fiducial markers 25 rigidly attached thereto. Passive or active signals emitted from the fiducial markers 25 are detectable by the tracking system 30 (e.g. a stereoscopic tracking system employing two tracking cameras). A sufficient number of tracking markers are provided to facilitate the determination of the position and orientation of the trackable surface detection device in three dimensions.

In one example implementation, the tracking subsystem 30 may include stereo cameras with an integrated light source for illuminating passive tracking marker spheres. The passive tracking marker spheres are localized in each image of the stereo cameras. These image positions may be employed to calculate the 3D position of each tracking marker by geometrical triangulation. If at least three tracking markers are rigidly attached to an object in a known configuration, detection of reflected signals from the tracking markers facilitates the determination of the position and orientation of the object (six degrees of freedom). In some example embodiments described herein, the tracking markers detectable by the tracking system are shown as reflective spheres, which are commonly used for passive optical tracking. However, any other type of markers, or marker attributes, can be used depending on the used tracking system such as, but not limited to LEDs, which do not require integration of additional lighting, reflective spheres, glyphs, varying marker color, varying marker size, varying marker shape. It is to be understood that in some embodiments, less than three markers may be employed for position tracking. For example, a single marker may be provided for position and orientation tracking, provided that the single marker includes sufficient spatial structure and/or content. An example of such a single marker is a glyph including co-planar spatial features such as corner or edge features.

As shown in FIG. 1, the tracking system 30 may also be employed to detect the position and orientation of a trackable medical instrument 40 having one or more fiducial markers 45 provided thereon. In an alternative example embodiment, the position and orientation of a medical instrument may be tracked via a surface detection subsystem 10, such as a structured light detection system, that is employed to detect the surface profile of a of at least a portion of the medical instrument, or structure attached thereto, and to determine the position and orientation of the medical instrument via comparison of the detected surface profile with a known surface profile.

Although not shown in FIG. 1, a tracked reference frame (e.g. a clamp with one or more reference markers provided thereon or attached thereto) may be attached to the patient and may be tracked by the tracking system 30.

As noted above, the reference surface 20 (an example of a reference feature) is positioned within the field of view 12 of the surface detection system (e.g. the field of view of the one or more cameras of a structured light surface detection subsystem), such that the surface detection subsystem 15 is capable of acquiring reference surface data from the reference surface 20. Although not shown in FIG. 1, the reference surface 20 has sufficient three-dimensional structure to facilitate a determination of its location and orientation based on surface data detected by the surface detection subsystem 15. For example, the reference surface 20 (which may be a plurality of reference surfaces) may include geometrical features such as pyramids, cubes, steps or chamfers.

It is noted that the previously known approach for determining a calibration transform, based on the use of a physically separate calibration device having a reference surface and tracking markers, requires the use of a reference surface having a three-dimensional profile that is capable of detection, by the surface detection system, from a wide variety of viewing orientations and illumination conditions. In contrast, according to the present example embodiments in which a reference feature is integrated with the surface detection subsystem in a spatially fixed configuration, the reference feature is provided in a known orientation relative to the surface detection system.

In the case of the reference feature being a reference surface, this known orientation may facilitate the use of simpler three-dimensional surfaces with fewer three-dimensional features and may improve registration quality. Furthermore, in example implementations in which the reference surfaces is at least partially residing within a housing of the trackable surface detection system, the housing may shadow the reference surface from external light sources, which may also facilitate the use of simpler three-dimensional surfaces with fewer three-dimensional features and may improve registration quality.

The example trackable surface detection device 10, which illustrates the use of a reference surface, is shown having the reference surface 20 defining an exit aperture of the device. However, it will be understood that the reference surface 20 may be incorporated at other locations relative to the surface detection subsystem, provided that it is rigidly supported relative to the surface detection subsystem 15, and resides, at least in part, within a field of view of the surface detection subsystem. It will also be understood that more than one reference surface may be integrated with the trackable surface detection device 10.

Figure 2A:
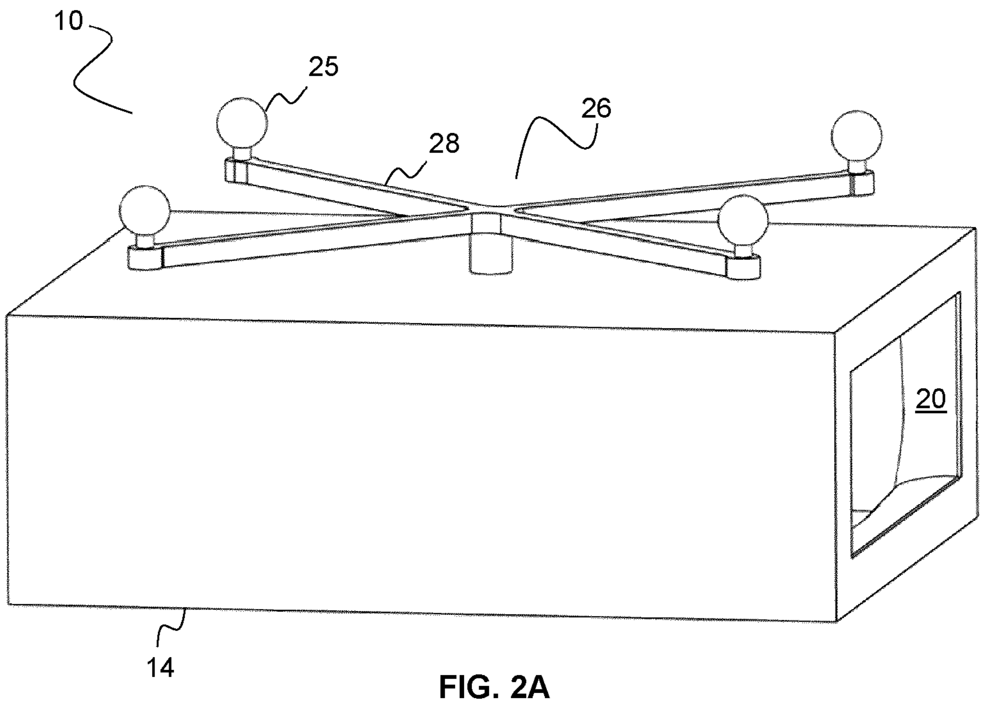
FIGS. 2A-2D illustrates an example implementation of a trackable surface detection device having an integrated reference surface for calibration.
Figure 2B:
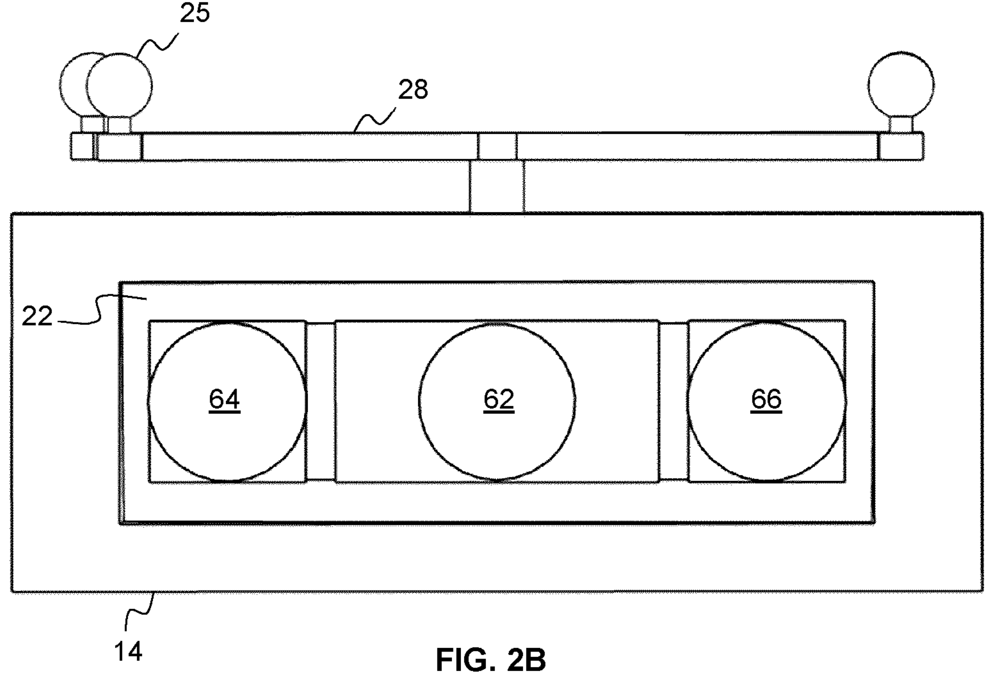
Figure 2C:
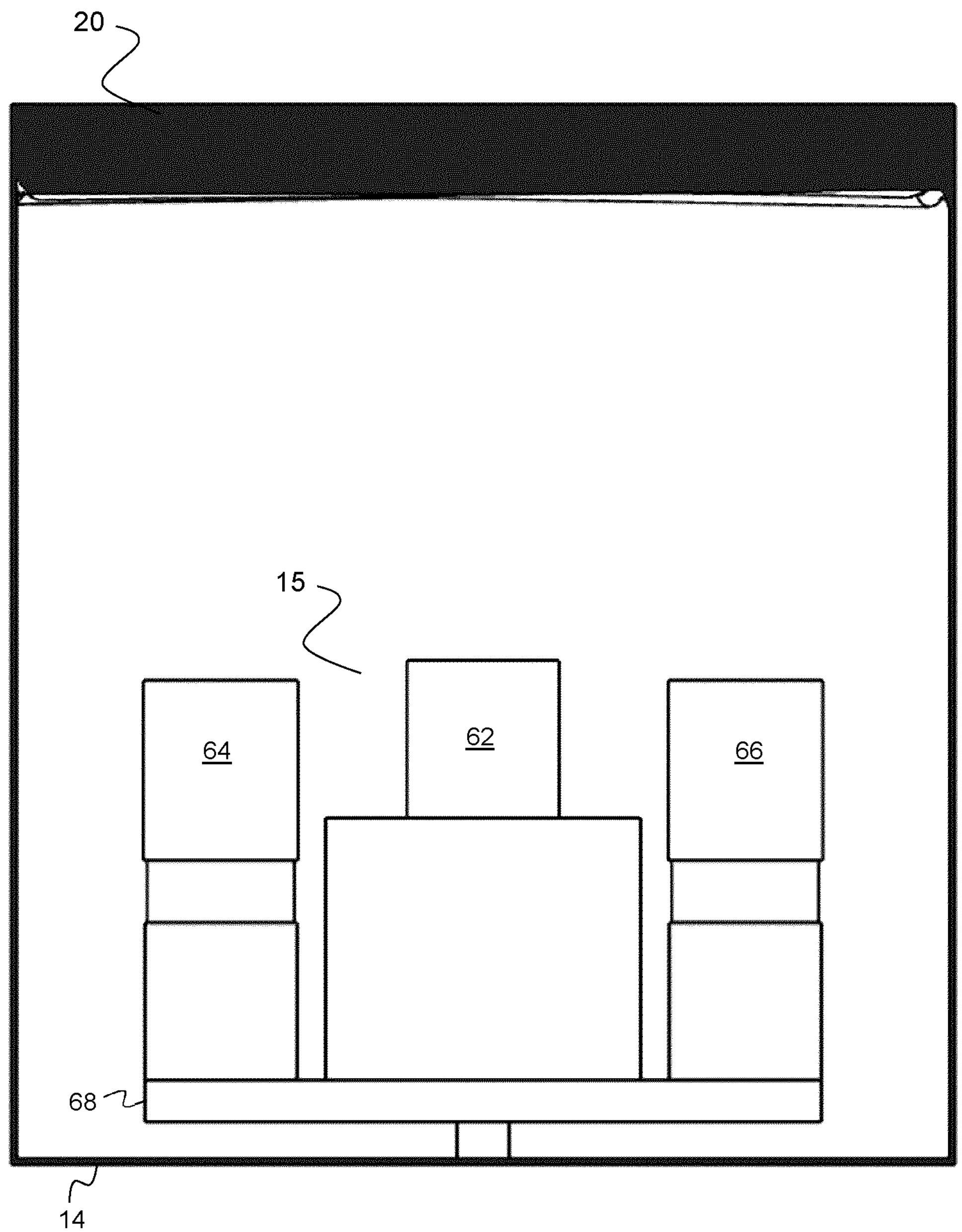

Referring now to FIGS. 2A-2C, an example implementation of a trackable surface detection device 10 is shown. The trackable surface detection device 10, which may be employed in a handheld configuration, includes a housing 14, a tracking marker assembly 26 having a plurality of passive tracking markers 25, and a tracking marker support structure 28 rigidly attached or connected to the housing 14. The housing supports the surface detection subsystem 15, which is shown in FIGS. 2B and 2C, such that the surface detection subsystem 15 is rigidly secured relative to the tracking markers 25. As shown in the figure, the surface detection subsystem 15 may include several components that are mounted on a common platform that is secured to the housing 14.

The example surface detection system 15 includes a structured light projector 62 and a pair of cameras 64 and 66 positioned to have a field of view capable of imaging structured light patterns that are projected, through the distal aperture 22 of the housing 14, onto an external object (such as an exposed anatomical region of a subject).

The example trackable surface detection device 10 includes an integrated reference surface 20. At least a portion of the reference surface resides within the field of view of the surface detection subsystem 15. In the present example implementation, the field of view of the surface detection subsystem 15 is determined according to the spatial overlap between the respective fields of view of cameras 64 and 66 and the spatial region within which the structured light is projected. As noted above, the example embodiments described herein may be practiced according to a wide variety of surface detection modalities. The field of view that is associated with a given implementation, using a given surface detection modality, may be readily determined via simulation and/or via performing experimental measurements.

In some example implementations, the reference feature may at least partially reside within a subregion of the field of view of the surface detection system, such as a subregion associated with a depth of field of the surface detection system. For example, a depth of field of a surface detection system may be determined according to the region spanned by the depths of field of the respective components forming the system. In the example case of a surface detection subsystem, the depth of field may be determined based on the respective depths of field of the cameras and optionally based on a depth of field associated with the projector's ability to project images according to a threshold resolution.

While the example embodiment shown in FIGS. 2A and 2B illustrates the tracking markers as being indirectly rigidly secured relative to the surface detection subsystem 15, through the tracking marker support structure 28 and the housing 14, it will be understood that one or more tracking markers 25, or the tracking marker support structure 28, may alternatively be directly secured to one or more components of the surface detection subsystem 15. Similarly, it will be understood that the reference surface 20 may alternatively be directly secured to one or more components of the surface detection subsystem 15.

Figure 2D:
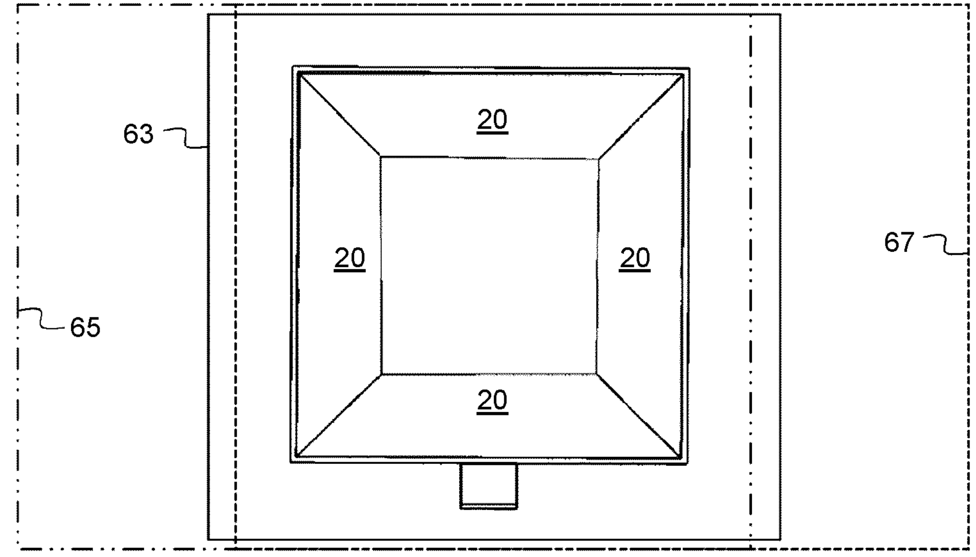

In the example implementation shown in FIGS. 2A-2C, the reference surface 20 is illustrated surrounding a distal aperture 22 of the housing 14. FIG. 2D presents a view from the perspective of the structured light subsystem, along the optical axis of the structured light subsystem, toward the reference surface 20 and distal aperture 22. The figure also shows the overlap of the respective fields of view 65 and 67 of the cameras (64 and 66 as shown in FIGS. 2B and 2C) and the spatial region 63 within which structured light from the projector is projected (e.g. the projected field of the projector). The field of view of the example structured light subsystem may be determined to be the intersection of the regions 63, 65 and 67.

It will be understood that the positioning of the reference surface as illustrated in FIGS. 2A-2C provides but one example implementation of many possible configurations in which a reference feature resides within field of view of the surface detection subsystem. In some example embodiments, a portion of the reference surface peripherally surrounds the distal aperture of the housing. In some example embodiments, a portion of the reference surface peripherally surrounds only a portion of the distal aperture of the housing. In some example embodiments, the entirety of the reference surface resides within the housing. In some example embodiments, the entirety of the reference feature resides beyond a distal aperture of the housing. In some example embodiments, at least a portion of the reference feature resides within the housing. In some example embodiments, at least a portion of the reference feature resides beyond a distal aperture of the housing.

Figure 3A:
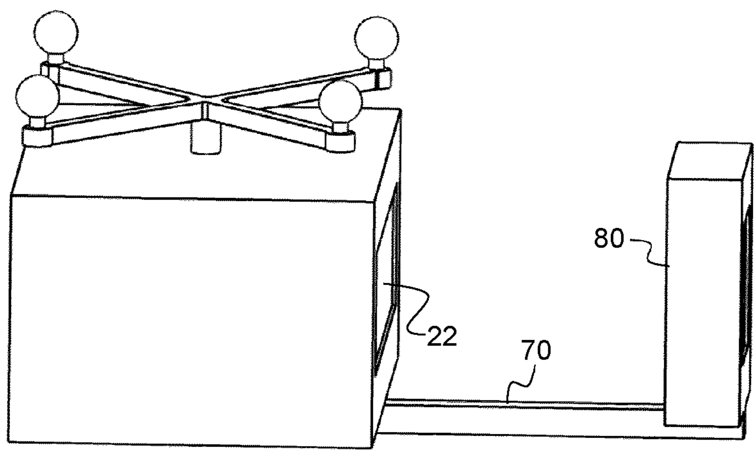
FIGS. 3A-3D illustrate an example implementation in which the reference surface is supported beyond the distal aperture of the housing, within the field of view of the surface detection subsystem.
Figure 3B:
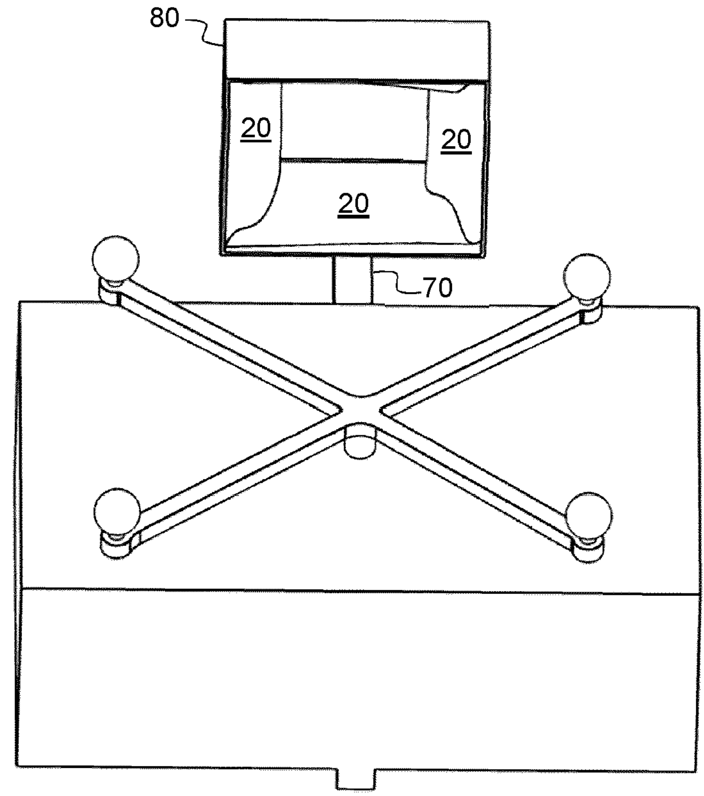
Figure 3C:
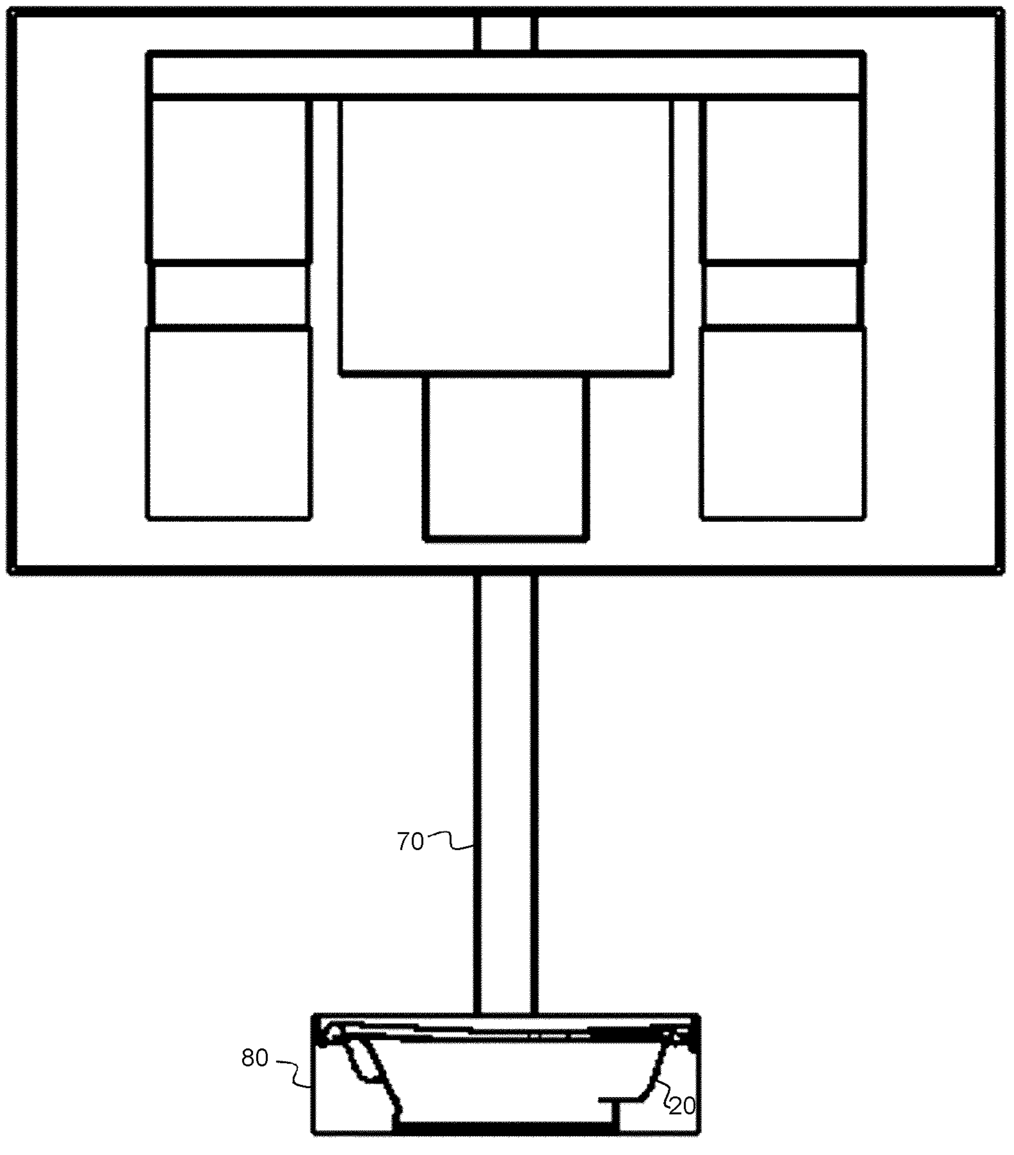
Figure 3D:
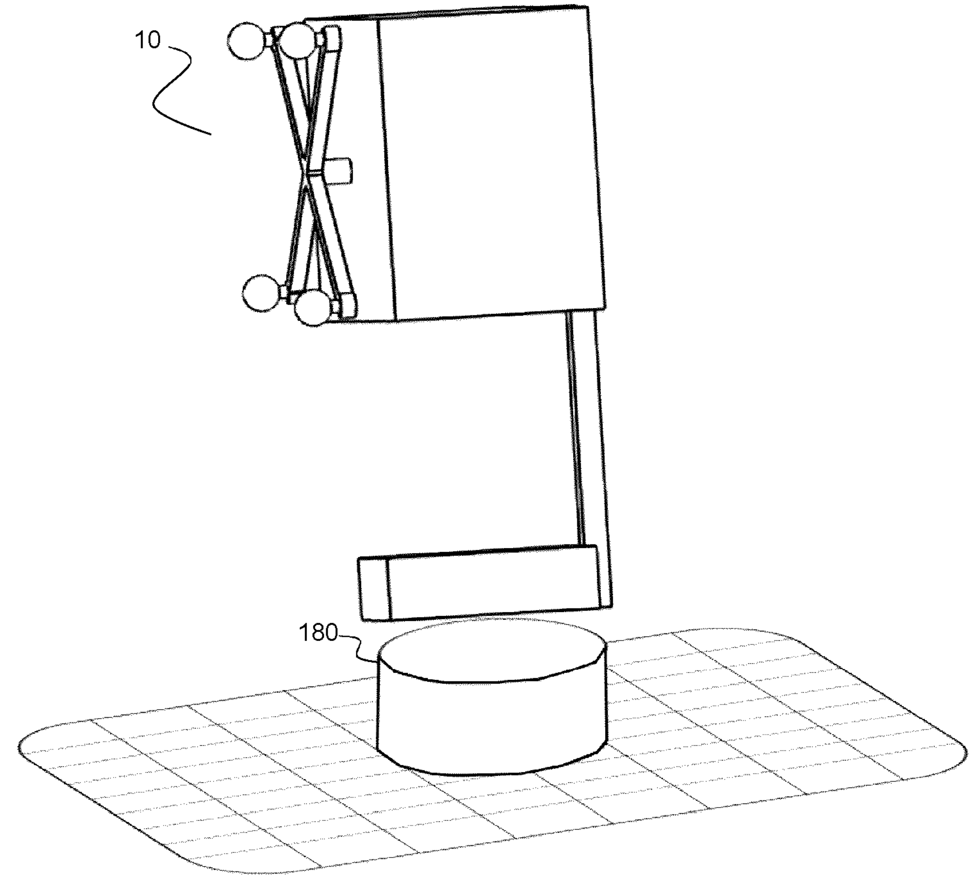

FIGS. 3A-3D illustrate an example implementation in which the reference surface 20 is supported beyond the distal aperture 22 of the housing, within the field of view of the surface detection subsystem. In the example implementation shown, the reference surface 20 is supported by a distal frame 80. The distal frame 80 is positioned distalward from the distal aperture 22 via a distal support member 70. FIG. 3D illustrates the use of a handheld trackable surface detection device 10 for performing intraoperative surface detection of an anatomical surface of a subject that is exposed through a surgical port 180. The trackable surface detection device 10 is positioned such that the field of view of the surface detection subsystem 10 extends to the exposed anatomical surface within the surgical port 180.

It will be understood that the surface detection modality used for the detection of external surface data (e.g. surface data that is associated with a subject and acquired intraoperatively) need not be the same as the detection modality used for the detection of the reference feature. For example, one or more cameras of the surface detection subsystem may be employed to detect one or more reference features, optionally in the absence of the characterization of a surface topography associated with the reference feature, using, for example, a detection modality such as photogrammetry or stereographic detection of fiducial markers.

Figure 4:
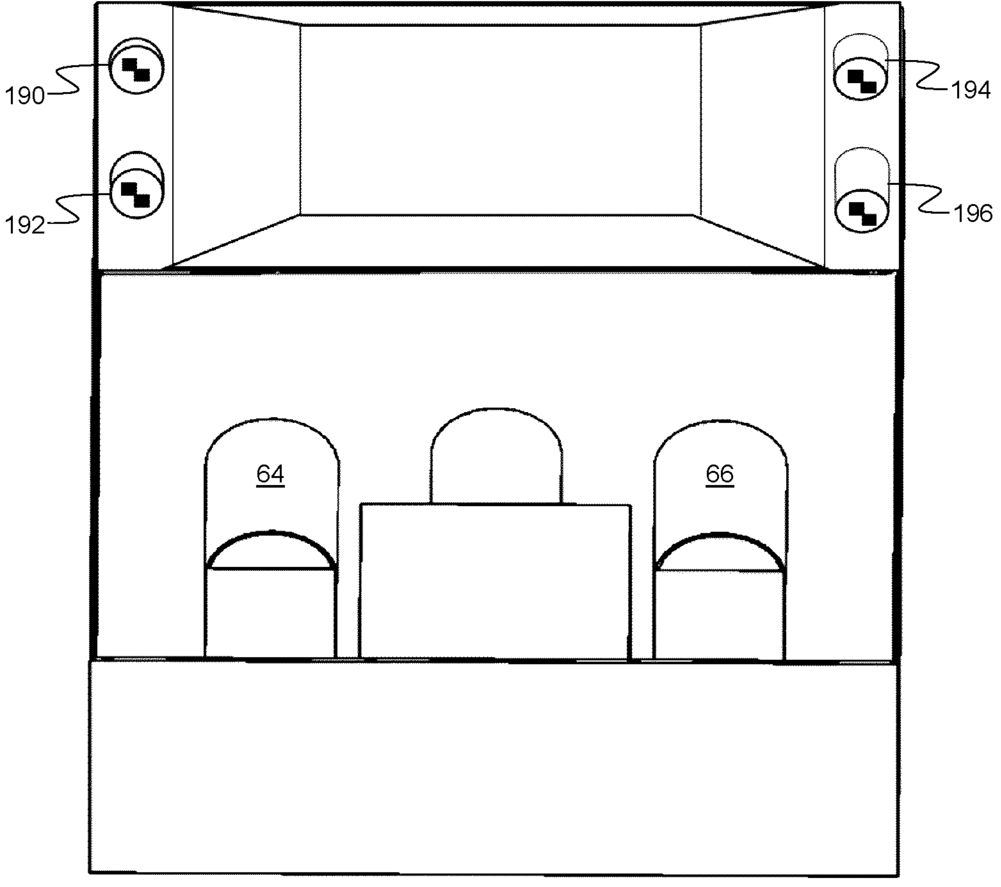
FIG. 4 illustrates an example embodiment in which a set of fiducial markers, detectable by the cameras of the surface detection system, are integrated within the trackable surface detection device.

An example implementation of such an embodiment is illustrated in FIG. 4, which shows an integrated surface detection device that employs reference fiducial markers as reference features. In the non-limiting example implementation shown in the figure, a set of reference fiducial markers 190, 192, 194 and 196 are provided that are visible by the camera system (within the field of view of the cameras 64 and 66). In the present example implementation, the fiducial markers 190-196 can be located through the use of corner detection. As shown in the figure, the fiducial markers can be provided such that they do not lie in a single plane, thereby enabling a unique 3D calibration to be generated. The fiducial markers can be detected, for example, by the stereo cameras of the surface detection subsystem, in the absence of surface detection of the fiducial markers, prior, during or immediately after the acquisition of surface data from an external surface. Such an embodiment may be advantageous in that the field of view of the illumination or projection component of the surface detection subsystem (e.g. a scanning laser or a structured light projector) need not overlap with the reference features (fiducial markers), which may be beneficial by increasing the illumination intensity on the external surface and potentially reducing the time duration required for the acquisition of surface data.

Figure 5:
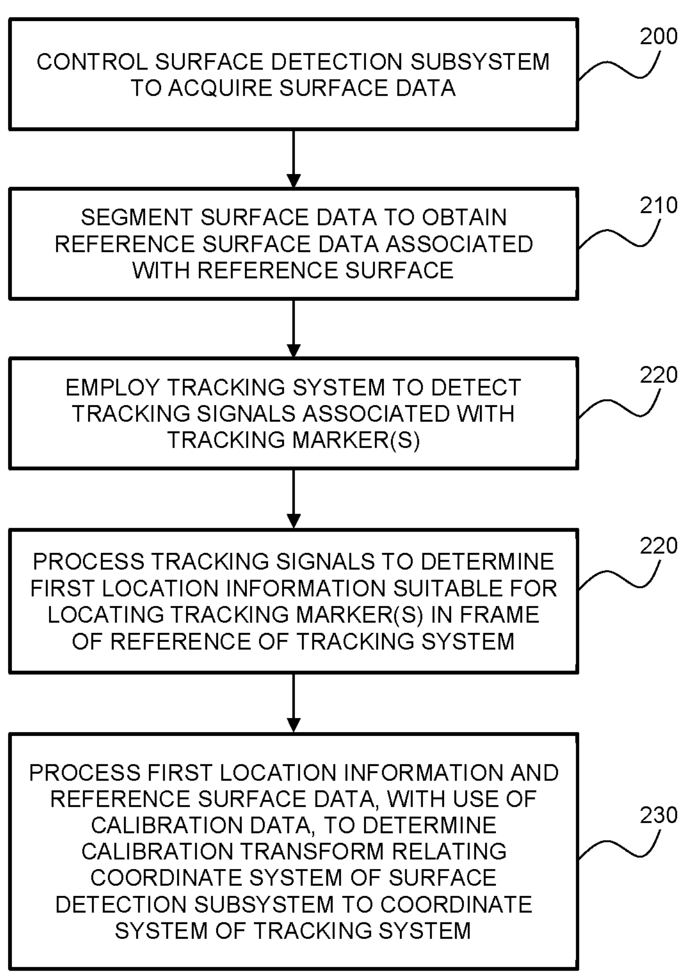
FIG. 5 is a flow chart illustrating an example method of performing intraoperative surface detection and intraoperative image registration for surgical navigation using a trackable surface detection device.

Referring now to the flow chart provided in FIG. 5, an example method is provided for determining a calibration transform based on the use of a reference surface integrated into a trackable surface detection device. As shown at step 200, the trackable surface detection device is employed to acquire surface data via control of the surface detection subsystem. This surface data includes reference surface data associated with the reference surface, since the reference surface resides, at least in part, within the field of view of the surface detection subsystem.

The surface data may be optionally segmented to obtain reference surface data associated with the reference surface, as shown at 210. The segmentation of the surface data to obtain the reference surface data may optionally be performed, for example, based on the known approximate location of the reference surface relative to the surface detection subsystem. This location can be employed to determine a suitable region within which to segment the acquired surface image data.

As shown at 220, the tracking system is employed to detect tracking signals associated with tracking marker(s) that are rigidly secured to trackable surface detection device. The tracking signals are processed to determine first location information that is suitable for locating the tracking marker (s) in the frame of reference of the tracking system, as shown at 230. For example, the first location information may prescribe the locations of each of the reference markers. Alternatively, the first location information may provide a location and orientation associated with the tracking marker assembly, or, for example, associated with another component or structure of the trackable surface detection device.

As shown at 240, the first location information, the surface data (optionally segmented) are then processed, with the use of calibration data, to determine the calibration transform that relates the coordinate system of the surface detection subsystem to the coordinate system of the tracking system. The calibration data includes three-dimensional model data characterizing the reference surface and second location information that is suitable for locating the reference surface relative to the at least one tracking marker. The three-dimensional model data may be provided, for example, mathematically in a functional form, or for example, via a point cloud or other data structure suitable for representing a three-dimensional structure. The second location information is based on the known spatial relationship between the reference surface and the tracking marker(s), which both rigidly supported within and/or on the trackable surface detection device. The second location information is sufficient to provide a spatial mapping between the known location of the reference surface and the location tracked by the tracking system.

The determination of the calibration transform, based on processing the first location information (facilitating location of the tracking markers within the frame of reference of the tracking system), the surface data, the three-dimensional model characterizing the reference surface, and the second location information (suitable for relating the known location of the reference surface to the known location of the tracking marker(s)), maybe be performed according to a variety of methods.

In some example methods, the calibration transform is determined, at least in part, by performing surface-to-surface registration between the three-dimensional model data and the (optionally segmented) surface data. It will be understood that any suitable surface registration method may be employed to perform registration between surfaces, when performing methods according to the example embodiments disclosed herein. Non-limiting examples of suitable registration methods include the iterative closest point algorithm, wherein the distance between points from difference surfaces are minimized.

In a first example implementation, the calibration transform may be determined by employing the first location information and the second location information to represent the three-dimensional model data within the coordinate system of the tracking system and performing surface-to-surface registration between the surface data and the three-dimensional model data (represented within the coordinate system of the tracking system). According to such an example implementation, the transform obtained from the surface-to-surface registration process is the calibration transform. The surface registration may be supported by an initial alignment step, in which the two surfaces (the surface data and the three-dimensional model data) are approximately aligned. In the present example implementation, this initial alignment step may be facilitated by selecting a first set of points within the surface data and a second set of points within the three-dimensional model data, with each point in the first set of points having a corresponding point in the second set of points.

In a second example implementation, the calibration transform may be determined by representing the three-dimensional model data and the surface data within an initial coordinate system that is fixed relative to a frame of reference of the trackable handheld surface detection device, and performing surface-to-surface registration between the surface data and the three-dimensional model data within the initial coordinate system, to obtain a preliminary calibration transform. The preliminary calibration transform provides a mapping between the coordinate system of the surface detection subsystem (within which the acquired surface data is represented) and the initial coordinate system that is fixed relative to the frame of reference of the trackable handheld surface detection device. The first location information, the preliminary calibration transform, and the second location information may then be employed to determine the calibration transform, since the first location and the second location information facilitate the generation of the mapping from the initial coordinate system to the coordinate system of the tracking system.

In the present example implementation, the three-dimensional model data may be initially aligned with the reference data, within the initial coordinate system, based on a known location of the reference surface relative to the surface detection subsystem (which may be provided as third location information). For example, the initial coordinate system may be the coordinate system of the surface detection system (i.e. the coordinate system employed to represent the surface data collected by the surface detection system), and the known location of the reference surface relative to the surface detection subsystem may be employed to represent, and roughly align, the three-dimensional model data with the surface data. The preliminary transform obtained from surface-to-surface registration represents the correction between the actual and the expected location of the surface data associated with the reference surface. This preliminary transform, when combined with the second location information (suitable for relating the known location of the reference surface to the known location of the tracking marker(s)) and with the first location information (facilitating location of the tracking markers within the frame of reference of the tracking system), enables the determination of the calibration transform.

While the preceding example method, and the method illustrated in the flow chart shown in FIG. 5, have been described in the context of the detection of reference surface data associated with a reference surface, it will be understood that a calibration transform may alternatively be determined based on the detection of one or more reference features other than a reference surface. For example, one or more reference features (such as the fiducial markers shown in FIG. 4) may be detected using one or more cameras of the surface detection subsystem, thereby providing reference signals, and the detected reference signals may be processed, along with the detected tracking signals and calibration data, to determine the calibration transform that relates the coordinate system of the surface detection subsystem to the coordinate system of the tracking system. The calibration data includes model data characterizing the reference feature and second location information that is suitable for locating the reference feature relative to the at least one tracking marker. The model data may be provided, for example, mathematically in a functional form, or for example, via a point cloud or other data structure suitable for representing a the reference feature. The second location information is based on the known spatial relationship between the reference feature and the tracking marker(s), which both rigidly supported within and/or on the trackable surface detection device. The second location information is sufficient to provide a spatial mapping between the known location of the reference feature and the location tracked by the tracking system.

During a medical (e.g. surgical) procedure, the trackable surface detection device (optionally in a handheld configuration) is positioned and oriented such that the relevant exposed three-dimensional anatomical surface of subject (e.g. the surgical site, such as an exposed bony surface) resides within the field of view of the trackable surface detection device, and the trackable surface detection device is controlled to acquire surface data. Surface-to-surface registration between the surface data and pre-operative surface data (segmented from pre-operative volumetric image data associated with the subject) is employed to determine an intraoperative transform. The calibration transform and the intraoperative transform are then employed to facilitate the display of the pre-operative image data and one or more tracked surgical tools (tracked by the tracking system) within a common frame of reference.

The surface-to-surface registration may be performed using any suitable registration method, such as, but not limited to, those described above, optionally guided by initial picking of corresponding points within the surface data and the pre-operative surface data. The pre-operative surface data may be segmented from the pre-operative volumetric image data according to a wide variety of methods. One example method involves selecting a suitable threshold and generating an isosurface using the marching cubes algorithm from the volumetric image data. Another example is to construct an isocontour from each 2D slice of a volumetric image data based on a suitable threshold, and stitching the slices together into a 3D surface.

In one example implementation, the tracking signals are detected when the surface tracking data is acquired (e.g. such that the time of tracking signal acquisition overlaps with the time of surface data acquisition), with the surface data being employed for performing both (i) the surface-to-surface registration step, performed during generation of the calibration transform, that involves the registration of surface data with the three-dimensional model data and (ii) the surface-to-surface registration step, performed to generate the intraoperative transform that involves the registration of surface data and pre-operative surface data. Such an example implementation facilitates the generation of an accurate calibration transform when acquiring surface data.

In an alternative implementation, the surface data that is employed during generation of the calibration transform (involving surface-to-surface registration between the surface data and the three-dimensional model data) may be acquired separately from, and prior to, surface data that is employed during the surface-to-surface registration step that is performed to generate the intraoperative transform (involving the registration of surface data and pre-operative surface data). In such an example implementation, the tracking signals that are employed for the generation of the calibration transform are detected when the later acquired surface data (employed to generate the intraoperative transform) is acquired (e.g. such that the time of tracking signal acquisition overlaps with the time of surface data acquisition), and the initial surface data may be acquired asynchronously with the acquisition of the tracking signals. Such an example implementation obviates the need for surface-to-surface registration of surface data and the three-dimensional model data when generating the intraoperative transform.

In some example implementations, the trackable surface detection device may include a motion sensor that is capable of generating a signal indicative of the presence and/or magnitude of motion. Non-limiting example of motion sensors include accelerometers and gyroscopes. The motion sensor signal from the motion sensor may be processed by the control and processing circuitry, optionally to determine a measure associated with the sensed motion (e.g. vibration amplitude, velocity, acceleration). The motion sensor signal, or a measure derived therefrom, may be compared with pre-selected criteria to determine whether or not the motion is excessive (e.g. beyond a prescribed threshold). In the event that excessive motion is detected during acquisition of surface data (and/or tracking signals), the acquired data can be rejected and an indication may be provided in a user interface that the be surface data needs to be re-acquired.

In some example implementations, the trackable surface detection device may be capable of signaling, to one or both of the control and processing circuitry and the tracking system, when surface data acquisition is taking place. For example, one or more optical emitters located on the trackable surface detection device may be activated to indicate the acquisition of surface data. Alternatively, for example, an electrical signal may be delivered to one or both of the tracking system and the control and processing circuitry to indicate the acquisition of surface data. The detected signal may be employed, for example, to synchronize the detection of tracking signals with the acquisition of surface data.

Referring again to FIG. 1, an example implementation of control and processing circuitry 100 is shown, which includes one or more processors 110 (for example, a CPU/microprocessor), bus 105, memory 115, which may include random access memory (RAM) and/or read only memory (ROM), a data acquisition interface 120, a display 125, external storage 130, one more communications interfaces 135, a power supply 140, and one or more input/output devices and/or interfaces 145 (e.g. a speaker, a user input device, such as a keyboard, a keypad, a mouse, a position tracked stylus, a position tracked probe, a foot switch, and/or a microphone for capturing speech commands).

It is to be understood that the example system shown in FIG. 1 is illustrative of a non-limiting example embodiment, and is not intended to be limited to the components shown. Furthermore, one or more components of control and processing circuitry 100 may be provided as an external component that is interfaced to a processing device. For example, as shown in the figure, the tracking system 30 may be included as a component of control and processing circuitry 100 (as shown within the dashed line 101), or may be provided as one or more external devices.

Although only one of each component is illustrated in FIG. 1, any number of each component can be included in the control and processing circuitry 100. For example, a computer typically contains a number of different data storage media. Furthermore, although bus 105 is depicted as a single connection between all of the components, it will be appreciated that the bus 105 may represent one or more circuits, devices or communication channels which link two or more of the components. For example, in personal computers, bus 105 often includes or is a motherboard. Control and processing circuitry 100 may include many more or less components than those shown.

Control and processing circuitry 100 may be implemented as one or more physical devices that are coupled to processor 110 through one of more communications channels or interfaces. For example, control and processing circuitry 100 can be implemented using application specific integrated circuits (ASICs). Alternatively, control and processing circuitry 100 can be implemented as a combination of circuitry and software, where the software is loaded into the processor from the memory or over a network connection.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete circuitry components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Embodiments of the present disclosure can be implemented via processor 110 and/or memory 115. For example, the functionalities described below can be partially implemented via circuitry logic in processor 110 and partially using the instructions stored in memory 115. Some embodiments are implemented using processor 110 without additional instructions stored in memory 115. Some embodiments are implemented using the instructions stored in memory 115 for execution by one or more microprocessors, which may be general purpose processors or specialty purpose processors. Thus, the disclosure is not limited to a specific configuration of circuitry and/or software.

The control and processing circuitry 100 is programmed with subroutines, applications or modules 150, which include executable instructions, which when executed by the one or more processors 110, causes the system to perform one or more methods described in the present disclosure. Such instructions may be stored, for example, in memory 115 and/or other internal storage. In particular, in the example embodiment shown, calibration and registration module 155 includes executable instructions for generating a calibration transform based on surface data associated with the reference surface 20 (or a reference feature) and for registering surface data (obtained from the volumetric image data 35) with intraoperative surface data according to the methods disclosed herein. The navigation user interface module 160 may include executable instructions for displaying a user interface for performing, for example, image-guided surgical procedures.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A trackable surface detection device comprising:

a surface detection subsystem configured to acquire surface data characterizing surface topography within a field of view;

a reference feature positioned and rigidly secured within the field of view of said surface detection subsystem such that the surface data acquired by said surface detection subsystem comprises reference surface data associated with said reference feature;

at least one tracking marker, wherein said surface detection subsystem, said reference feature and said at least one tracking marker are rigidly secured such that a fixed spatial relationship is defined between said at least one tracking marker, said surface detection subsystem, and said reference feature; and a computer-readable medium comprising calibration data, the calibration data comprising:

three-dimensional model data characterizing the reference feature, the three-dimensional model data being configured such that a position and orientation of said reference feature is determinable based on registration of the three-dimensional model data and the reference surface data; and first location information for locating said reference surface relative to said at least one tracking marker;

the calibration data facilitating determination of a calibration transformation between a frame of reference of the surface detection subsystem and a frame of reference of a tracking system based on detection of the reference surface data by the surface detection system and detection of the at least one tracking marker by the tracking system.

2. The surface detection device according to claim 1 further comprising a housing, said housing supporting said surface detection subsystem.

3. The surface detection device according to claim 2 wherein said housing is configured to be supported in a handheld configuration.

4. The surface detection device according to claim 2 wherein at least a portion of said reference feature is rigidly supported within said housing.

5. The surface detection device according to claim 2 wherein a distal region of said housing includes an aperture, and wherein at least a portion of said reference feature is peripherally disposed around at least a portion of said aperture.

6. The surface detection device according to claim 2 wherein at least a portion of said reference feature is rigidly supported beyond a distal end of said housing.

7. The surface detection device according to claim 2 wherein said reference feature is rigidly supported beyond a distal end of said housing.

8. The surface detection device according to claim 2 wherein said surface detection subsystem has a depth of field for surface detection that resides, at least in part, beyond a distal end of said housing, and wherein said reference feature resides within the depth of field of said surface detection subsystem.

9. The surface detection device according to claim 1 wherein said surface detection subsystem is a structured light surface detection subsystem.

10. The surface detection device according to claim 1 wherein said reference feature comprises a reference surface detectable by said surface detection subsystem.

11. A medical navigation system comprising:

a trackable surface detection device provided according to claim 10;

a tracking system configured to detect said at least one tracking marker;

control and processing circuitry operatively coupled to said surface detection subsystem and said tracking system, said control and processing circuitry comprising at least one processor and associated memory, said memory comprising instructions executable by said at least one processor for performing operations comprising:

controlling said tracking system and said surface detection subsystem to:

acquire surface data; and detect tracking signals associated with said at least one tracking marker;

processing the tracking signals to obtain second location information suitable for locating said at least one tracking marker within a coordinate system of said tracking system; and processing the second location information, the surface data, and the calibration data, to determine the calibration transform.

12. The medical navigation system according to claim 11 wherein said control and processing circuitry is configured to generate the calibration transform by:

employing the first location information and the second location information to represent the three-dimensional model data within the coordinate system of said tracking system; and performing surface-to-surface registration between the surface data and the three-dimensional model data represented within the coordinate system of said tracking system, thereby obtaining the calibration transform.

13. The medical navigation system according to claim 12 wherein said control and processing circuitry is configured to:

segment the surface data to obtain reference surface data associated with said reference surface; and employ the reference surface data when performing surface-to-surface registration.

14. The medical navigation system according to claim 11 wherein said control and processing circuitry is configured to generate the calibration transform by:

representing the three-dimensional model data and the surface data within an initial coordinate system that is fixed relative to a frame of reference of said trackable surface detection device;

within the initial coordinate system, performing surface-to-surface registration between the surface data and the three-dimensional model data, thereby obtaining a preliminary calibration transform; and employing the first location information, the preliminary calibration transform, and the second location information to determine the calibration transform.

15. The medical navigation system according to claim 14 wherein the initial coordinate system is the coordinate system of said surface detection subsystem.

16. The medical navigation system according to claim 11 wherein the surface data and the tracking signals are obtained simultaneously, and wherein said control and processing circuitry is further configured to:

employ surface-to-surface registration between (i) the surface data and (ii) pre-operative surface data generated from pre-operative volumetric image data associated with a subject, to determine an intraoperative transform; and employ the intraoperative transform and the calibration transform to represent the pre-operative volumetric image data and one or more tracked medical instruments within a common frame of reference.

17. The medical navigation system according to claim 11 wherein the surface data is first surface data, wherein said control and processing circuitry is further configured to:

acquire second surface data simultaneously with acquisition of the tracking signals;

employ surface-to-surface registration between (i) the second surface data and (ii) pre-operative surface data generated from pre-operative volumetric image data associated with a subject, to determine an intraoperative transform; and employ the intraoperative transform, and the calibration transform to represent the pre-operative volumetric image data and one or more tracked medical instruments within a common frame of reference.

18. The medical navigation system according to claim 11 wherein said trackable surface detection device further comprises a motion sensor, said motion sensor being operatively coupled to said control and processing circuitry, wherein said control and processing circuitry is further configured to:

process motion sensor signals obtained from said motion sensor; and reject the calibration transform when the motion sensor signals, or a measure associated therewith satisfy motion criteria.

19. The medical navigation system according to claim 11 wherein said trackable surface detection device further comprises a means for signaling, to one or both of said tracking system and said control and processing circuitry, the acquisition of the surface data.

20. A surgical navigation system comprising:

a tracking system; and a trackable surface detection device according to claim 1;

wherein said at least one tracking marker is detectable by said tracking system.

21. A method of calibrating a surgical navigation system, the surgical navigation system comprising a trackable surface detection device according to claim 10 and a tracking system, the method comprising:

controlling the trackable surface detection device to acquire surface data;

controlling the tracking system to detect tracking signals associated with the at least one tracking marker of the trackable surface detection device;

processing the tracking signals to obtain second location information suitable for locating the at least one tracking marker within a coordinate system of the tracking system; and processing the first location information, the surface data, and calibration data, to determine the calibration transform.

22. The method according to claim 21 wherein the calibration transform is generated by:

employing the first location information and the second location information to represent the three-dimensional model data within the coordinate system of the tracking system; and performing surface-to-surface registration between the surface data and the three-dimensional model data represented within the coordinate system of the tracking system, thereby obtaining the calibration transform.

23. The method according to claim 22 further comprising:

segmenting the surface data to obtain reference surface data associated with the reference surface; and employing the reference surface data when performing surface-to-surface registration.

24. The method according to claim 21 wherein the calibration transform is generated by:

representing the three-dimensional model data and the surface data within an initial coordinate system that is fixed relative to a frame of reference of the surface detection device;

within the initial coordinate system, performing surface-to-surface registration between the surface data and the three-dimensional model data, thereby obtaining a preliminary calibration transform; and employing the first location information, the preliminary calibration transform, and the second location information to determine the calibration transform.

25. The method according to claim 24 wherein the initial coordinate system is the coordinate system of the surface detection subsystem.

26. The method according to claim 21 wherein the surface data and the tracking signals are obtained simultaneously, the method further comprising:

employing surface-to-surface registration between (i) the surface data and (ii) pre-operative surface data generated from pre-operative volumetric image data associated with a subject, to determine an intraoperative transform; and employing the intraoperative transform and the calibration transform to represent the pre-operative volumetric image data and one or more tracked medical instruments within a common frame of reference.

27. The method according to claim 21 wherein the surface data is first surface data, the method further comprising:

acquiring second surface data simultaneously with acquisition of the tracking signals;

employing surface-to-surface registration between (i) the second surface data and (ii) pre-operative surface data generated from pre-operative volumetric image data associated with a subject, to determine an intraoperative transform; and employing the intraoperative transform, and the calibration transform to represent the pre-operative volumetric image data and one or more tracked medical instruments within a common frame of reference.

28. A medical navigation system comprising:

a trackable surface detection device provided according to claim 1;

a tracking system configured to detect said at least one tracking marker;

control and processing circuitry operatively coupled to said surface detection subsystem and said tracking system, said control and processing circuitry comprising at least one processor and associated memory, said memory comprising instructions executable by said at least one processor for performing operations comprising:

controlling said surface detection subsystem to acquire reference signals associated with said reference feature; and controlling said tracking system to detect tracking signals associated with said at least one tracking marker;

processing the tracking signals to obtain second location information suitable for locating said at least one tracking marker within a coordinate system of said tracking system; and processing the second location information, the reference signals, and calibration data, to determine the calibration transform.

29. The medical navigation system according to claim 28 wherein said surface detection subsystem is a structured light surface detection system comprising a projector and one or more cameras, and wherein the reference signals are detected by said one or more cameras in absence of illumination by said projector.

30. A method of calibrating a surgical navigation system, the surgical navigation system comprising a trackable surface detection device according to claim 1 and a tracking system, the method comprising:

controlling the trackable surface detection device to acquire reference signals associated with said reference feature;

controlling the tracking system to detect tracking signals associated with the at least one tracking marker of the trackable surface detection device;

processing the tracking signals to obtain second location information suitable for locating the at least one tracking marker within a coordinate system of the tracking system; and processing the second location information, the reference signals, and calibration data, to determine the calibration transform.

* * * * *